(12) United States Patent
Scandolera et al.

(10) Patent No.: US 11,654,102 B2
(45) Date of Patent: May 23, 2023

(54) COSMETIC COMPOSITION COMPRISING VETIVER ROOT EXTRACT

(71) Applicant: GIVAUDAN SA, Vernier (CH)

(72) Inventors: Amandine Scandolera, Reims (FR); Carole Lambert, Cugnaux (FR); Romain Reynaud, Toulouse (FR)

(73) Assignee: GIVAUDAN SA, Vernier (CH)

( * ) Notice: Subject to any disclaimer, the term of this patent is extended or adjusted under 35 U.S.C. 154(b) by 66 days.

(21) Appl. No.: 16/968,267

(22) PCT Filed: Mar. 11, 2019

(86) PCT No.: PCT/EP2019/056008
§ 371 (c)(1),
(2) Date: Aug. 7, 2020

(87) PCT Pub. No.: WO2019/175094
PCT Pub. Date: Sep. 19, 2019

(65) Prior Publication Data
US 2021/0030663 A1 Feb. 4, 2021

(30) Foreign Application Priority Data
Mar. 12, 2018 (GB) ..................................... 1803883

(51) Int. Cl.
| | | |
|---|---|---|
| *A61K 36/00* | (2006.01) | |
| *A61K 8/9794* | (2017.01) | |
| *A61Q 19/00* | (2006.01) | |
| *A61Q 19/08* | (2006.01) | |
| *C07C 49/733* | (2006.01) | |
| *C07C 49/743* | (2006.01) | |
| *C07C 49/747* | (2006.01) | |
| *C07C 61/35* | (2006.01) | |
| *C07C 62/32* | (2006.01) | |
| *C07D 303/32* | (2006.01) | |
| *C07D 303/38* | (2006.01) | |

(52) U.S. Cl.
CPC .......... *A61K 8/9794* (2017.08); *A61Q 19/007* (2013.01); *A61Q 19/08* (2013.01); *C07C 49/733* (2013.01); *C07C 49/743* (2013.01); *C07C 49/747* (2013.01); *C07C 61/35* (2013.01); *C07C 62/32* (2013.01); *C07D 303/32* (2013.01); *C07D 303/38* (2013.01); *A61K 2236/331* (2013.01); *C07C 2602/32* (2017.05)

(58) Field of Classification Search
CPC .............................. A61Q 19/08; A61Q 19/007
See application file for complete search history.

(56) References Cited

U.S. PATENT DOCUMENTS

| | | |
|---|---|---|
| 6,193,976 B1 | 2/2001 | Porras et al. |
| 2012/0142570 A1 | 6/2012 | Surianarayanan et al. |

FOREIGN PATENT DOCUMENTS

| | | | |
|---|---|---|---|
| DE | 10325159 A1 | | 12/2003 |
| JP | H0761918 A | | 3/1995 |
| JP | 2007291031 A | | 11/2007 |
| JP | 2011236174 A | * | 11/2011 |
| SU | 821483 A1 | | 4/1981 |
| WO | 2010086728 A1 | | 8/2010 |

OTHER PUBLICATIONS

Kadarohman et al, Biolarvicidal of Vetiver Oil and Ethanol Extract of Vetiver Root Distillation Waste (Vetiveria zizanoides) Effectiveness toward Aedes aegypti, *Culex* sp., and Anopheles sundaicus Journal of essential oil-bearing plants (2013), pp. 749-762 (Year: 2013).*
International Search Report and Written Opinion of the International Searching Authority for corresponding application PCT/EP2019/056008 dated May 6, 2019.
GB Search Report for corresponding application GB 1803883.6 dated Oct. 24, 2018.
Junju Xu et al: "Eremophilane-Type Sesquiterpenes From Alpinia oxyphylla With Inhibitory Activity Against Nitric Oxide Production", Chemistry of Natural Compounds, Jul. 1, 2013, pp. 390-393.
Database GNPD Mintel; anonymous: "Youth Cleanse Daily Exfoliating Cleanser", Aug. 24, 2015, XP055577919, retrieved from www.gnpd.com, Database accession No. 3431063 abstract.
Database GNPD Mintel, anonymous: "Face Cleanser", Dec. 14, 2015 XP055577912, retrieved from www.gnpd com, Database accession No. 3652833 abstract.
Database GNPDMINTEL; anonymous: "Shaving Foam", Feb. 13, 2017, XP055577892, retrieved from www.gnpd.com, Database accession No. 4606327 abstract.
Database GNPD Mintel, anonymous: "Advanced Whitening Xtra Moisturize Nourishing Face & Body Lotion", Oct. 18, 2016 , XP055577890, retrieved from www.gnpd.com, Database accession No. 4340055 abstract.
Database GNPD Mintel; anonymous: "White Tea Jasmine Feather-Light Face Cream", Dec. 22, 2015, retrieved from www.gnpd.com, Database accession No. 3571373 abstract.
Yoshinori Asakawa et al: "Modification of Valencene by Bio- and Chemical Transformation", Natural Product Communications, vol. 8, No. 7, Jul. 1, 2013.

* cited by examiner

*Primary Examiner* — Qiuwen Mi
(74) *Attorney, Agent, or Firm* — Norris McLaughlin PA (57) ABSTRACT

A cosmetic composition is provided, which comprises a carrier and a Vetiver root extract, in particular an extract from exhausted Vetiver root. This composition provides a stimulation of sebum production, stimulation of sebum antimicrobial, lipids production, activation of adipocytes volume increase, skin hydration, skin tonicity booster, skin fatigue reduction, perilabial wrinkles reduction, skin replumping, and fragrance long-lastingness enhancement.

4 Claims, 7 Drawing Sheets

Figure 1

(*** p<0.001 Student's t test)

Figure 2

(* p<0.05    ** p<0.01 Student's t-test    # p<0.01 Student's t-test)

Figure 3

(* p<0.05    ** p<0.01 Student's t-test)

Figure 4

(*** p<0.001 Student's t test)

Figure 5

(** p<0.01 Student's t test)

Figure 6

(* p<0.05 Student's t test)

(* p<0.05 Student's t test)

COSMETIC COMPOSITION COMPRISING VETIVER ROOT EXTRACT

This is an application filed under 35 USC 371 based on PCT/EP2019/056008, filed 11 Mar. 2019, which in turn is based on GB 1803883.6 filed 12 Mar. 2018. The present application claims the full priority benefit of these prior applications and herein incorporates by reference the full disclosures of these prior applications.

The present invention relates to cosmetic compositions comprising a Vetiver root extract.

Vetiver (*Vetiveria zizanioides*, also *Chrysopogon zizanioides, Andropogon squarrosus*, or *Andropogon muricatus*) is a perennial bunchgrass of the Poaceae family, native to India.

Vetiver is mainly cultivated for the fragrant essential oil distilled from its roots, typically by steam distillation. Worldwide production is estimated at about 250 tons per annum. Due to its excellent fixative properties, vetiver is used widely in perfumes. It is contained in 90% of all western perfumes. Indonesia, China, and Haiti are major producers.

Vetiver essential oil is a complex oil, containing over 100 identified components, such as benzoic acid, furfurol, vetivene, vetivenyl vetivenate, terpinen-4-ol, 5-epiprezizane, khusimene, α-muurolene, khusimone, Calacorene, β-humulene, α-longipinene, γ-selinene, δ-selinene, δ-cadinene, valencene, calarene, α-gurjunene, α-amorphene, epizizanal, 3-epizizanol, khusimol, Iso-khusimol, valerenol, β-vetivone, α-vetivone, and vetivazulene.

The oil is amber brown and rather thick. Its odor is described as deep, sweet, woody, smoky, earthy, amber, and balsam. The roots are dug up, cleaned, and then dried. Before the distillation, the roots are chopped and soaked in water. The distillation process can take up to 24 hours. After distillation, the exhausted roots are usually discarded.

It is an aim of the present invention to add value to exhausted Vetiver roots.

This is achieved by the cosmetic compositions and methods of the present invention.

A brief description of the drawing is as follows.

In a first aspect, the present invention provides a cosmetic composition comprising a carrier and at least one active cosmetic ingredient, wherein a first active cosmetic ingredient comprises a Vetiver root extract.

In contrast to the essential oil obtained by distillation, the Vetiver root extract is obtained by extracting the Vetiver roots with a solvent.

The Vetiver root extract of the present invention is fully natural and odour-free.

Surprisingly, it was found that the Vetiver root extract of the present invention possesses impressive skin care properties and is able to reactivate the lipid synthesis in the skin.

In particular, it is able to stimulate sebum secretion both in an androgenic and a non-androgenic sebocyte model (see below). It was further found to increase neosynthesis of lipids on reconstructed human epidermis and to improve the structure of the epidermis on a model of skin explants. These observations are supported by a proteomic study (see below).

Therefore, in a particular embodiment, the cosmetic composition of the present invention is a skin care composition, in particular an anti-ageing composition. To this end, the carrier should be a dermatologically acceptable carrier.

A particularly suitable extract is an aqueous extract of Vetiver root. Therefore, in a preferred embodiment of the present invention, the first active cosmetic ingredient comprises an aqueous extract of Vetiver root.

The aqueous extract may be obtained by extracting Vetiver root with pure water. Optionally, the water may contain additives, e.g. for adjusting the pH.

Surprisingly, it was found that even the extraction of exhausted Vetiver root provided an active cosmetic ingredient having the advantageous effects described above. Therefore, in a particular embodiment of the present invention, the first active cosmetic ingredient comprises an extract of exhausted Vetiver root.

Throughout this application, the term "exhausted Vetiver root" refers to Vetiver root that has previously been processed by steam distillation. Thus, it refers to the remains of the root after the essential oil has been removed.

In a particular embodiment, the invention relates to an aqueous extract of exhausted Vetiver root. This allows for adding additional value to a "waste" product.

In a further aspect, the present invention relates to a method of preparing an active cosmetic ingredient, the method comprising extracting Vetiver root.

By extracting, it is meant that the Vetiver root is treated with a solvent or a mixture of solvents. The solvent(s) may also contain additives. For instance, the Vetiver root may be subjected to water extraction, acidic extraction, enzymatic extraction, ultrasound assisted water extraction, pressurized water extraction or ethanolic extraction.

Preferably, the Vetiver root is reduced to smaller pieces prior to the extraction, in particular cut and/or ground.

The Vetiver root may also be washed prior to the extraction. It was found that washing the root, in particular with water, led to a decreased color of the extract.

It was found that extraction with water, optionally containing one or more additives, provides the best results.

Suitable additives include, but are not limited to, acids, base, buffers, salts and/or co-solvents. In particular, the pH of the extraction solvent may be adjusted by the addition of acid (e.g. $H_2SO_4$ or citric acid) or base (e.g. NaOH).

It was found that the use of pure water (pH around 7.48 with roots), or of essentially pure water, was particularly advantageous.

Therefore, in one particular embodiment, the extraction is performed using pure water.

The extraction may be performed at room temperature or at elevated temperature, e.g. at a temperature of about 40° C., about 60° C., or about 80° C. It was found that a temperature of about 60° C. was particularly advantageous.

The Vetiver root extract may be purified, for example by filtration (e.g. on KDS15 filters), charcoal treatment and/or sterilizing filtration.

The Vetiver root extract may also be concentrated. It is possible to add 1,3-propanediol to the extract prior to concentration to improve the solubility of the extract during concentration.

In a particular embodiment, the method of the present invention comprises the steps of (i) providing exhausted Vetiver root; and (ii) extracting the exhausted Vetiver root.

Figure 1:
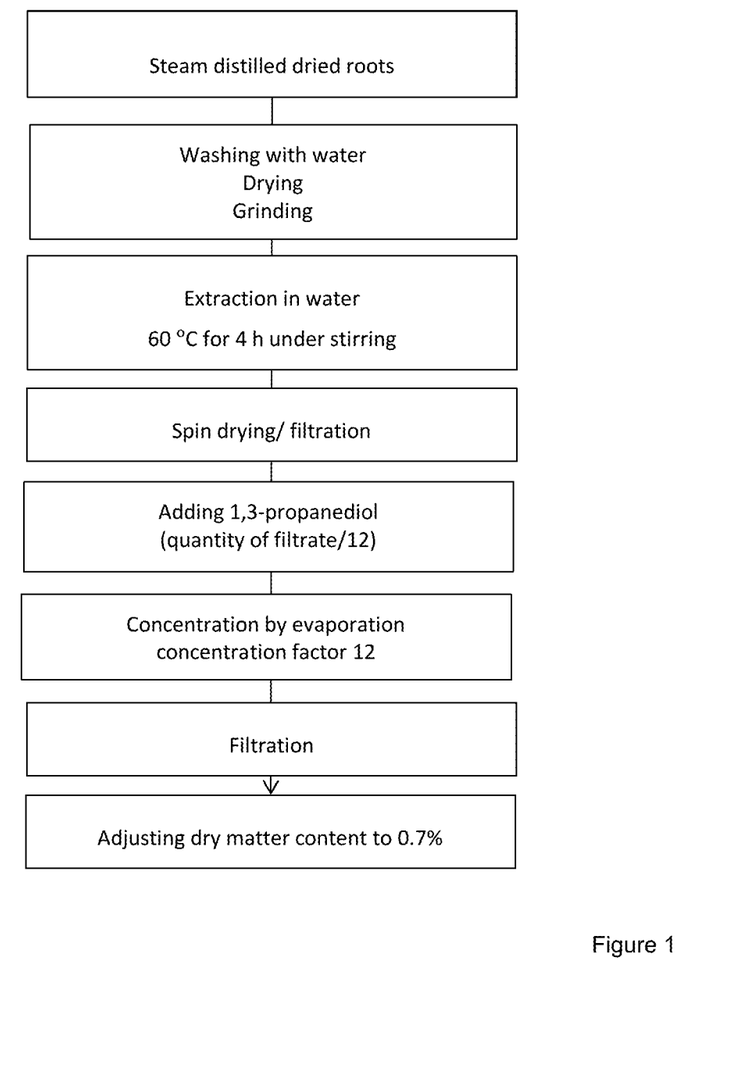
FIG. 1 shows a flow chart of an optimized extraction process, according to one or more embodiments of the present disclosure.

FIG. 1 shows a flow chart of the optimized extraction process. It involves the following steps:
(i) Providing steam distilled, dried Vetiver roots;
(ii) Washing the Vetiver roots with water, drying them, and grinding them;
(iii) Extracting the Vetiver roots with water at a temperature of 60° C. for 4 hours under stirring;
(iv) Spin drying the extract and filtration;
(v) Adding 1,3-propanediol (quantity of filtrate/12);
(vi) Concentration by evaporation by a concentration factor of 12;
(vii) Filtration; and
(viii) Adjusting the dry matter content to 0.7%.

The extracts obtained by this process typically have a zizanoic acid content of about 150 to about 250 mg/l, in particular about 250±20 mg/l; a pH of about 6.5 to about 7.5, in particular about 7.0±0.2; and a value of about 7.8 to about 9.1 on the Gardner Color Scale, in particular about 8.5±0.3. Color, pH, yield in zizanoic acid, and dry matter yield were found to be stable.

For analysis purposes, two batches were prepared according to the following procedure:
Extraction 75 g of washed roots in 2000 g of water 60° C. for 8 h
Filtration
Concentration 5 times (similar to FCM 12 propanediol)
Filtration
Sterilizing filtration
Freeze drying

A biphasic system MTBE/Acetonitrile/water (4/1/5; v/v) was used to fractionate 1.5318 g of extract in centrifugal partition chromatography. Elution was performed in ascending mode at flow rate 20 ml/min and rotation at 1200 rpm.

Upper phase was pumped through stationary phase during 70 minutes. Fractions 9 to 70 were collected. Extrusion was realized in descending mode, and corresponds to fractions 71-78.

Fractions were pooled in 13 groups according to similarity in TLC profile. TLC was performed with Machery nagel silica gel reversed phase and solvent ethyl acetate/toluene/acetic acid/formic acid (20/80/11/11).

The 13 groups were analyzed in $^1$H and $^{13}$C NMR and 2D experiments were recorded (HSQC, HMBC, COSY).

The following substances have thus been identified in the aqueous extract of exhausted Vetiver root:

(1)

(2)

(3)

(4)

(5)

The present invention thus also provides mixtures of two or more substances selected from (1) to (20), in particular mixtures of at least 5 of these substances, more particularly of at least 10 of these substances, and most particularly of all of the substances (1) through (20).

One key component of the extract of the present invention is zizanoic acid, a previously reported sesquiterpene having structure (1). Also some of the other metabolites have been previously described, for instance oplopanone (6), solanerianone A (8), vetiverianine B (10), valencene-11,12-diol (12), isovalencenic acid (13), and teuhetenone (15).

Substances (2), (3), (4), (5), (7), (9), (11), and (14), on the other hand, have never been described before.

Therefore, in a further aspect, the present invention also relates to a chemical substance selected from the group consisting of

(2)

(3)

(4)

(5)

(7)

(9)

(11)

(14)

Surprisingly, it was found that the solubility of zizanoic acid in water is improved by the other substances present in the extract of the present invention.

The cosmetic composition of the present invention displayed impressive skin care properties, as will be shown below.

Skin lipids play a fundamental role in the maintenance of skin hydration, suppleness and barrier function. They are mostly produced by three types of cells:

Sebocytes, located in the sebaceous glands, produce sebum, a thin lipidic film primarily composed of triglycerides, wax esters, squalene, and free fatty acids. Sebum ensures the skin protection from dehydration, the maintenance of its suppleness and also protects skin microflora by its acidic pH and its Antimicrobial Lipids (AML).

Keratinocytes accumulate lipids during their differentiation, such as ceramides and cholesterol derivatives, which will further build up the skin cornified envelope of the stratum corneum. This process is a key step in the preservation of skin barrier function and also prevents skin dehydration.

Adipocytes, present in the subcutaneous fat, produce other types of triglycerides for energy storing, mechanical protection and thermoregulation. They play an important role in skin volume, tonicity and firmness by ensuring mechanical support.

The disruption of the stratum corneum integrity usually starts with lipids depletion, with an overall decrease of −30% with age. Lipids produced by the sebocytes are also affected, with a gradual decrease of sebum production around 25% per decade. This results in a loss of hydration of the skin.

Meanwhile, facial fat loss upon ageing is related to a lower differentiation of the adipocytes, and a decreased fat storage, resulting in lower firmness and tonicity, sagging and wrinkles appearance.

The Vetiver root extract of the present invention acts on the three main lipids sources in the skin, improving the sebum production, the keratinisation and the adipocytes capacity to store fat. Three clinical tests versus placebo have highlighted the consumer benefits:
1. Improvement of skin hydration
2. Decrease of skin fatigue and reduction of wrinkles, specifically in the perilabial area
3. Fragrance enhancing properties In an ex vivo investigation study, the Vetiver root extract of the present invention was found to increase lipids production and thus improve the skin barrier function (see example 3 below).

The Vetiver root extract of the present invention also boosts the sebum quantity and quality (see example 4 below).

The reactivation of lipids production (in vitro/ex vivo) and the reactivation of skin barrier proteins (ex vivo) was also observed (see examples 5 and 6 below). This confirms the barrier function reconstruction.

The Vetiver root extract of the present invention was also found to boost skin adipocytes differentiation and size (see example 7 below).

In a clinical test, a visible skin fatigue reduction and decrease of perilabial wrinkles was observed (see example 8 below).

The composition of the present invention was also found to benefit the skin composition and hydration (see example 9 below).

The composition of the present invention was further found to possess fragrance boosting benefits (see example 10 below).

Thus, in conclusion, the composition of the present invention provides a stimulation of sebum production, stimulation of sebum antimicrobial, lipids production, activation of adipocytes volume increase, skin hydration, skin tonicity booster, skin fatigue reduction, perilabial wrinkles reduction, skin replumping, and fragrance long-lastingness enhancement.

Therefore, the composition of the present invention may be used in serums for dry skin, anti-aging perilabial serums, anti-aging night and day creams, anti-fatigue essences, skin tonifying masks, anti-acne creams, and body lotions for increasing fragrance long-lastingness.

In a further aspect, the present invention relates to the use of an extract from Vetiver root in skin care. This allows for exploiting the positive effects of the Vetiver root extract described above.

In a particular embodiment, an aqueous extract and/or an extract from exhausted Vetiver root is used.

The Vetiver root extract is particularly advantageously used in an anti-aging product.

In a further aspect, the present invention relates to a method of stimulating the sebum production, of stimulating sebum antimicrobials, of stimulating the lipids production, of activating the adipocytes volume increase, of improving the skin hydration, of boosting the skin tonicity, of reducing skin fatigue, of reducing perilabial wrinkles, of replumping skin, and/or of enhancing fragrance long-lastingness by applying the cosmetic composition of the present invention to human skin.

The present invention is further illustrated by means of the following non-limiting examples:

EXAMPLE 1: PREPARATION OF VETIVER ROOT EXTRACT FOR IN VITRO AND EX VIVO STUDIES

Exhausted *Vetiveria zizanioides* roots from Haiti (75 g) were suspended in water (2000 g). Extraction was performed under stirring at 60° C. for 4 h. The pH was monitored during extraction and varied from about 7.4 to about 7.8.

After filtration, the solution was concentrated by water removal until it reached a final dry matter content of 0.7%. The product is typically a limpid dark yellow to amber liquid with no smell, and has a pH of about 7.7 to 7.8. This extract is typically used for in vitro and ex vivo studies.

For the studies described in the subsequent examples, aqueous solutions containing 1%, 2% and 3% of the extract, respectively, were prepared.

EXAMPLE 2: PREPARATION OF VETIVER ROOT EXTRACT FOR IN VIVO STUDIES

Exhausted *Vetiveria zizanioides* roots from Haiti (75 g) were suspended in water (2000 g). Extraction was performed under stirring at 60° C. for 4 h. The pH was monitored during extraction and varied from about 7.4 to about 7.8.

After filtration, 1,3-propanediol was added to the solution, and the resulting mixture concentrated by water removal until it reached a final dry matter content of 0.7%. The product is typically limpid dark yellow to amber liquid with no smell, and has a pH of about 6.5 to 7.5 This extract is typically used for in vivo studies.

For the studies described in the subsequent examples, aqueous solutions containing 2% of the Vetiver extract, respectively, were prepared.

For examples 8 and 9:

| INCI Name | Quantity (%) |
| --- | --- |
| AQUA/WATER | 88.65 |
| *Vetiveria zizanoides* root extract | 2.0 |
| CAPRIC/CAPRYLIC TRIGLYCERIDE | 4.5 |
| CETEARYL WHEAT STRAW GLYCOSIDES, CETEARYL ALCOHOL | 4.0 |
| PHENOXYETHANOL, METHYL PARABEN, PROPYL PARABEN, ETHYL PARABEN | 0.4 |
| DIMETHICONE | 0.3 |
| FRAGRANCE, HEXYL CINNAMAL, BUTYLPHENYL METHYLPROPIONAL, CITRONELLOL, ALPHA ISOMETHYL IONONE, HYDROXYISOHEXYL 3-CYCLOHEXENE CARBOXALDEHYDE | 0.1 |
| SODIUM HYDROXIDE | 0.05 |

For example 11:

| INCI Name | Quantity (%) |
| --- | --- |
| AQUA/WATER | 96.01 |
| ACRYLATES/C10-30 ALKYL ACRYLATE CROSSPOLYMER | 0.5 |
| PHENOXYETHANOL | 1 |
| *VETIVERIA ZIZANOIDES* ROOT EXTRACT, PROPANEDIOL, WATER | 2 |
| SODIUM HYDROXIDE | 0.49 |

EXAMPLE 3: INCREASING LIPIDS PRODUCTION FOR BARRIER FUNCTION (EX VIVO)

A proteomic analysis was performed by LC-MS/MS on human skin explants of three donors (54, 56 and 69 years old women) on which the 1% solution from the extract of example 1 was applied every day for six days. The results are shown in the following table:

| Cellular function | Protein | x fold expression |
|---|---|---|
| Lipids metabolism & transport | ORM1 - Alpha 1 acid glyco-protein 1 | 0.57* |
| | RTN4 - Reticulon-4 | 1.33* |
| | CLTA - Clathrin light chain A | 3.77* |
| | SNX5 - Sorting nexin 5 | 1.72* |
| | CERT - Ceramide transport protein | 2.69* |
| | TFG - Protein TFG | 1.34** |
| Epidermis differentiation | INV - Involucrin | 1.59 |
| | KRT36 - Keratin type I cuticular Ha6 | 1.73** |
| | DMKN - Dermokine | 1.53** |
| | LOR - Loricrin | 3.39* |

*$p < 0.05$ Student's t-test
**$p < 0.01$ Student's t-test

These results show that the extract of example 1 stimulates the expression of a complete set of proteins involved in the multiple pathways targeting lipids production, lipids transport, and epidermis differentiation. The composition improves the epidermal barrier through the modulation of lipid metabolism of the skin.

EXAMPLE 4: BOOSTING SEBUM QUANTITY AND QUALITY a) Sebocytes Stimulation (In Vitro)

Sebocytes were pre-incubated with the 1% solution from the extract of example 1 for 4 hours. Then, a lipogenic mix (vitamin C, vitamin D3, insulin and calcium) was added for another 7 days of incubation. Treatment was renewed after 3 days. The lipid content was then evaluated using Bodipy® fluorescent labeling (lipids were made visible in green).

Figure 2:
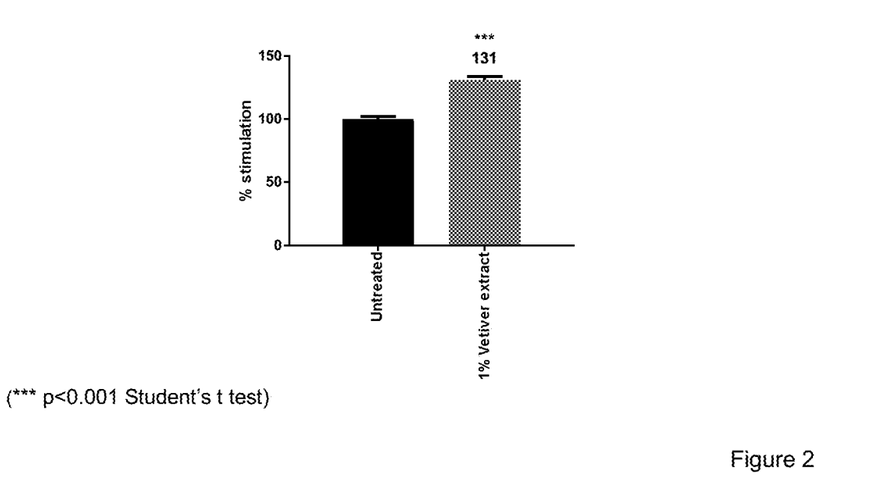
FIG. 2 shows a graph illustrating first comparative testing results for Example 4, according to one or more embodiments of the present disclosure.

The results are shown in FIG. 2. It was found that the extract of example 1 shows a significant stimulation of sebocytes, with an increase of sebum lipids accumulation of up to +31% versus lipogenic mix only.

b) Antimicrobial Lipids (AML) Content Increase (In Vitro)

Sebocytes were cultivated in 3D culture and treated in systemic with the 1% solution from the extract of example 1 for 7 days. The content of free fatty acids was then assessed by GC/MS to analyse their content in AML.

Figure 3:
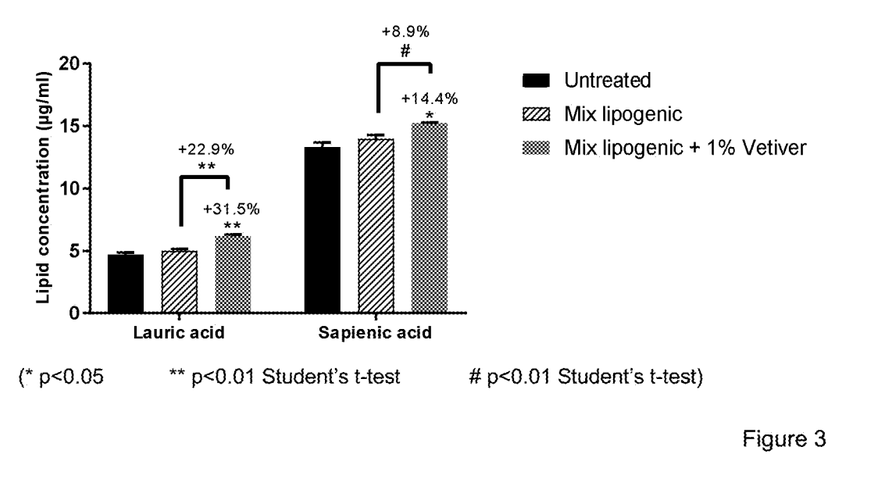
FIG. 3 shows a graph illustrating second comparative testing results for Example 4, according to one or more embodiments of the present disclosure.

The results are shown in FIG. 3. It was found that the extract of example 1 significantly increases the content of antimicrobial lipids in sebum (lauric acid and sapienic acid) by up to +23% compared to no treatment.

Figure 4:
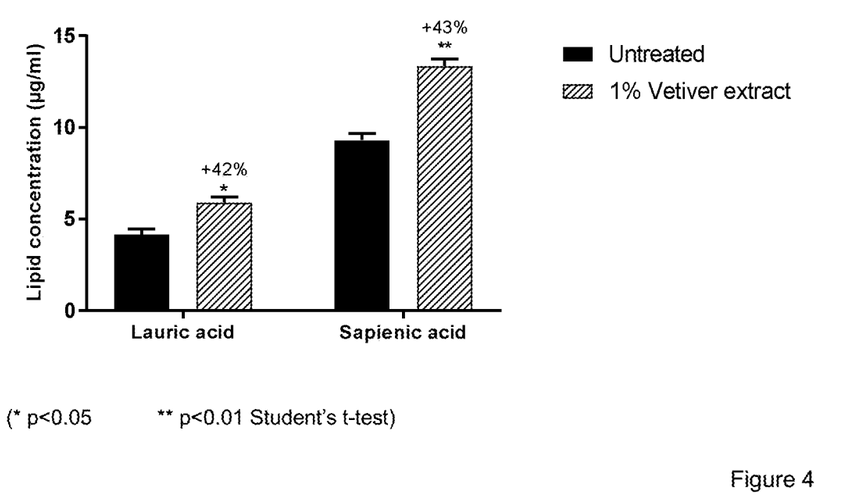
FIG. 4 shows a graph illustrating third comparative testing results for Example 4, according to one or more embodiments of the present disclosure.

The same experimental procedure was repeated without lipogenic mix stimulation. It was found that the Vetiver root extract is able to induce the production of anti-microbial lipids without any other lipogenic stimulation on sebaceous cells model (FIG. 4).

In particular, the Vetiver root extract significantly induced the production of lauric acid (+42%) and sapienic acid (+43%), both of which are considered as key AMLs.

EXAMPLE 5: BARRIER FUNCTION RECONSTRUCTION (IN VITRO): REACTIVATION OF LIPIDS PRODUCTION (IN VITRO/EX VIVO)

a) Ceramides and their Precursors Synthesis

Reconstructed Human Epidermis (RHE) was incubated with the 1% solution from the extract of example 1 for 7 days. Lipids contained in RHE were then extracted and studied by thin layer chromatography and densitometric analysis to assess the quantity of ceramide precursors in the RHE.

The results are shown in the following table:

| | Untreated | Vetiver 1% | p value (versus untreated) |
|---|---|---|---|
| Sphingomyelins | 100 | 142 | $p < 0.01$ |
| Phosphoglycerides | 100 | 138 | $p < 0.01$ |
| Ceramides series 1, polar lipids | 100 | 132 | $p < 0.01$ |

It was found that the extract of example 1 significantly increases the production of the ceramides and their various precursors in the epidermis by up to +42% compared to untreated RHE. Thus, the Vetiver extract has the ability to stimulate the neosynthesis of specific lipids in RHE.

b) Ceramides Transport Stimulation

Normal Human Keratinocytes (NHEKs) were stimulated for 5 days with the 1% solution from the extract of example 1. Ceramide Transport Protein (CERT) was then quantified by immunofluorescence.

Figure 5:
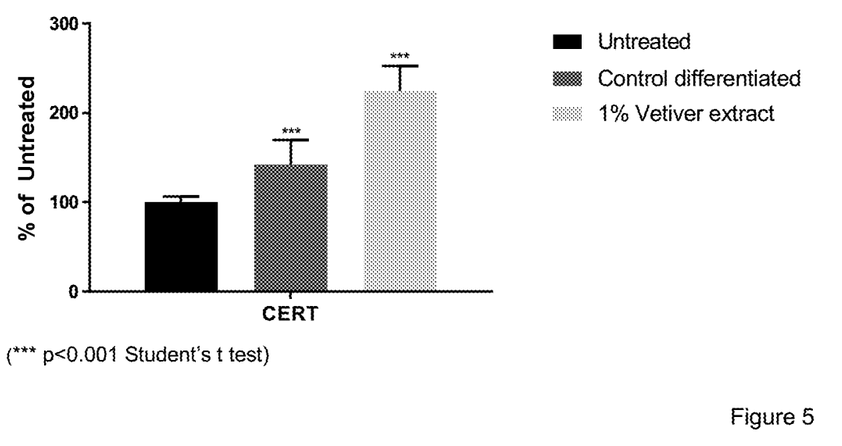
FIG. 5 shows a graph illustrating first comparative testing results for Example 5, according to one or more embodiments of the present disclosure.

The results are shown in FIG. 5. It was found that the extract of example 1 significantly increases the expression of CERT by up to +124.5% compared to untreated NHEKs, enabling a better transport of the lipids in the epidermis.

c) Boosting Lipids Content

Skin explants from a donor aged 69 were topically treated with the 1% solution from the extract of example 1 for 6 days. The neutral lipids from skin were stained using LipidTOX™. The immunostaining was quantified by microscopical observation (green fluorescence) to assess stimulation of keratinisation.

Figure 6:
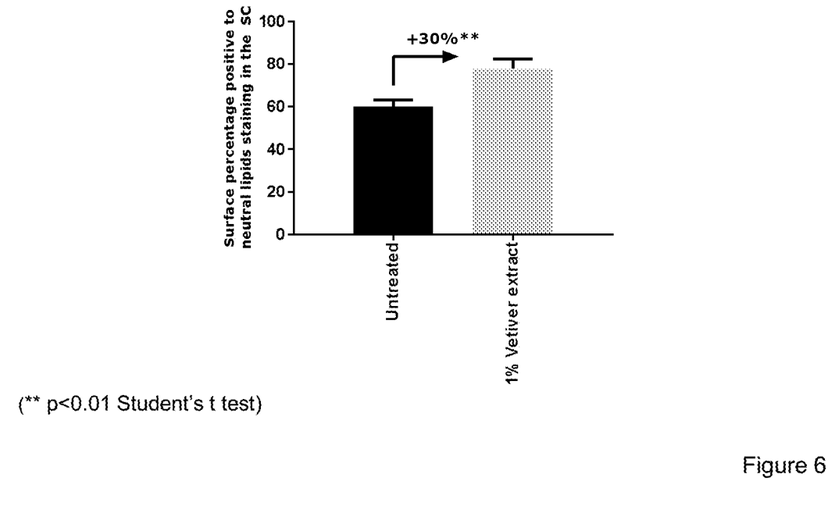
FIG. 6 shows a graph illustrating second comparative testing results for Example 5, according to one or more embodiments of the present disclosure.

The results are shown in FIG. 6. It was found that, as a result of boosting lipids production and transport, the extract of example 1 significantly increases the lipid content in the cornified envelope by up to +30% compared to untreated samples.

EXAMPLE 6: BARRIER FUNCTION RECONSTRUCTION (IN VITRO): REACTIVATION OF SKIN BARRIER PROTEINS (EX VIVO)

Human skin explants from three donors (54, 56 and 69 years old women) on which the 1% solution from the extract of example 1 was applied every day for 6 days were assessed by proteomic using LC-MS/MS for quantification of dermokine, involucrin and loricrin, three characteristic proteins of the cornified envelope.

Figure 7:
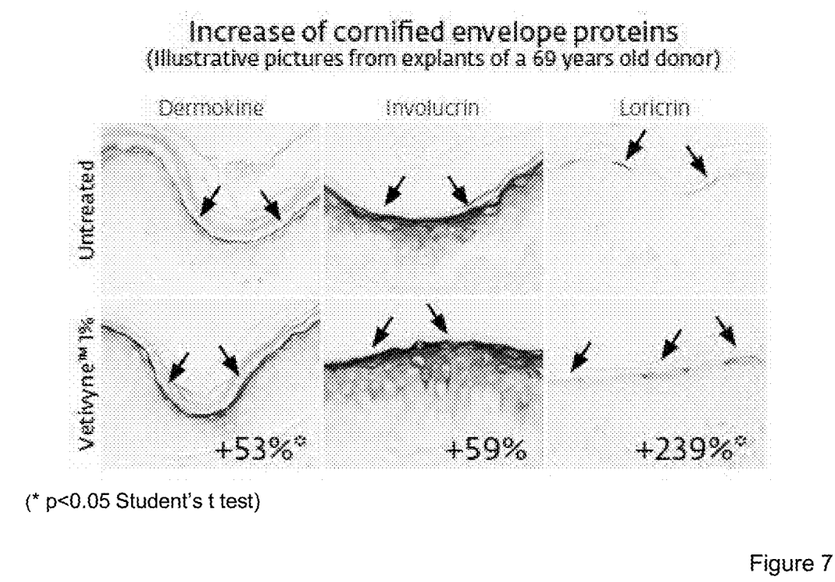
FIG. 7 shows illustrative pictures depicting comparative testing results for Example 6, according to one or more embodiments of the present disclosure.

The results are shown in FIG. 7. It was found that the extract of example 1 significantly increases the expression of these three major proteins of the stratum corneum, by +53% up to +239% in average. Thus, the Vetiver extract has a clear impact on the improvement of the epidermal barrier by reactivating the expression of these proteins, making the cornified envelope of the skin more cohesive.

EXAMPLE 7: BOOSTING SKIN ADIPOCYTES DIFFERENTIATION AND SIZE a) Improving Adipocytes Differentiation (In Vitro)

Pre-adipocytes were cultured for 13 days with the 3% solution from the extract of example 1. Lipid droplets, a marker of adipocytes differentiation, were then labelled using AdipoRed™ (a fluorescent lipid probe) to quantify the differentiation.

It was found that the extract of example 1 significantly increases the adipocytes differentiation, with an effect up to +3413% compared to untreated samples.

b) Increasing Adipocytes Volume (Ex Vivo)

Explants of full skin (epidermis, dermis, and hypodermis) were treated with the 3% solution from the extract of example 1. On D0, D1, D4 and D6, the product was topically applied. On D8, explants were stained for microscopical analysis. Adipocytes size determination was then performed by image analysis, by measuring their equivalent circular diameter.

It was found that the extract of example 1 significantly increases the average size of adipocytes in the hypodermis, as observed by microscopy.

It is also noticeable that a shift in the population of adipocytes can be observed after the use of the extract of example 1:

The number of "small" adipocytes (20-60 μm) increases by +26%, reflecting the differentiation boost observed in vitro (appearance of new small adipocytes from pre-adipocytes)

The number of "large" adipocytes (100-140 μm) increases by +189%, as a consequence of the average size increase and a better fat storage capacity (accumulation of lipids in the existing adipocytes)

During aging, the loss of adipose tissue volume is the consequence of an alteration of the fat tissue functions, such as the reduction of adipocyte size and changes in pre-adipocyte dynamics. As demonstrated by these two studies, the Vetiver extract has a beneficial impact on volume redefinition and acts as a "plumping" agent by reactivating the differentiation of pre-adipocytes and by stimulating the lipogenesis in mature adipocytes.

EXAMPLE 8: VISIBLE SKIN FATIGUE REDUCTION AND DECREASE OF PERILABIAL WRINKLES (CLINICAL TEST)

A double blind clinical evaluation was performed on two groups of 21 volunteers with sagging face and wrinkles (women from 52 to 69 years old, average of 60). Volunteers applied a placebo or the 2% solution from the extract of example 2 on their face for 56 days, twice a day (morning and evening).

a) Improvement of Tonicity/Firmness and Anti-Fatigue Effect

At D0, D28 and D56, skin biomechanical properties were measured by cutometry on cheekbones, focusing on the R6 and R9 parameters, respectively representative of the viscoelastic balance and of the fatigue effect. At D0, D28 and D56, face of the volunteers was analysed using AEVA HE®, a patented projection unit combined with stereo imaging.

Figure 8:
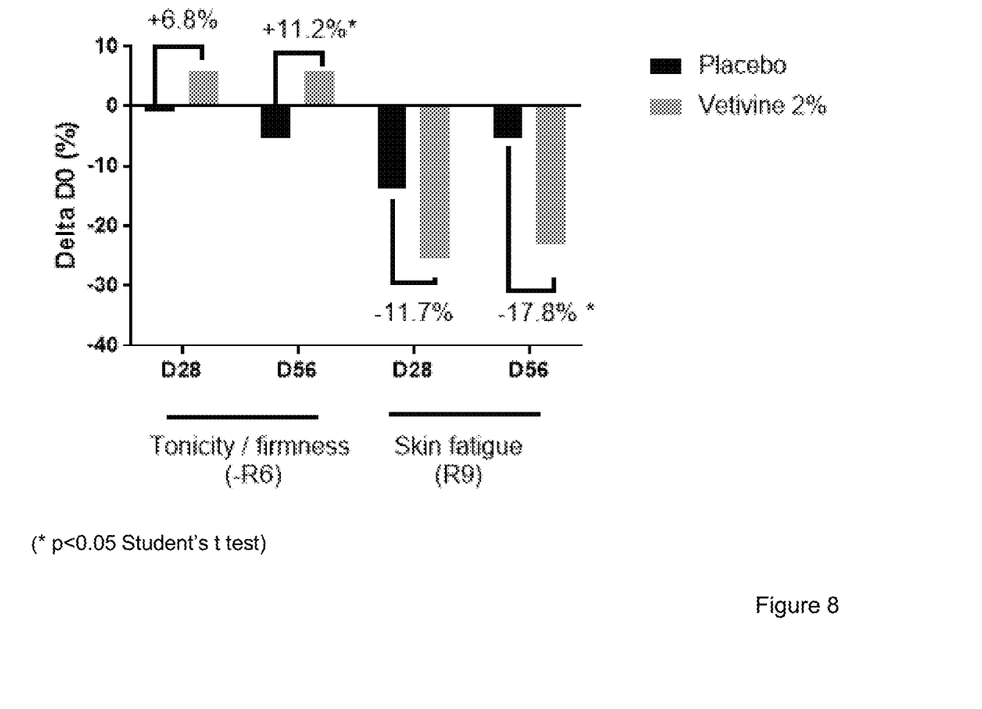
FIG. 8 shows a graph illustrating first comparative testing results for Example 8, according to one or more embodiments of the present disclosure.
Figure 9:
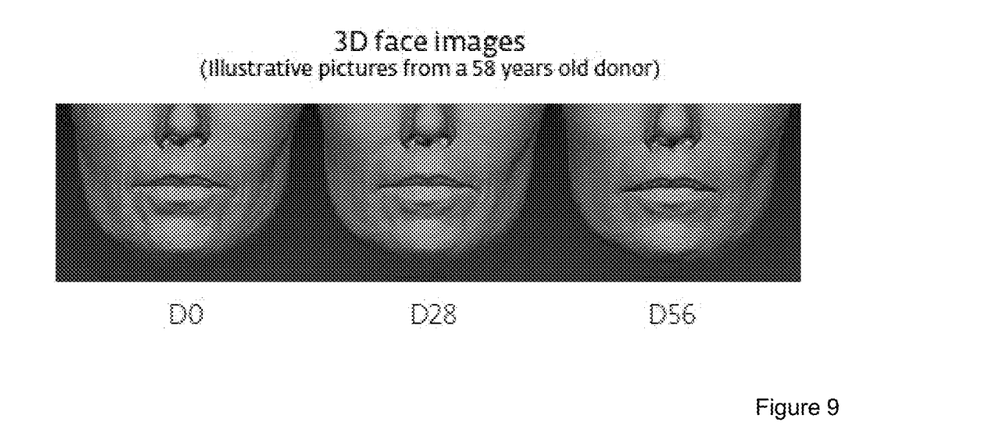
FIG. 9 shows 3D face images of volunteers illustrating second comparative testing results of Example 8, according to one or more embodiments of the present disclosure.

The results are shown in FIG. 8. The extract of example 2 enables a time-progressive and significant recovery of the skin biomechanical properties on aged volunteers, with up to +11.2% recovery in tonicity and firmness and −17.8% of skin fatigue decrease versus placebo. These results are also clearly visible on the 3D face images of the volunteers (FIG. 9).

b) Smoothing of Perilabial Wrinkles

At D0 and D56 a particular focus was put on the perilabial wrinkles of the volunteers to quantify them using AEVA HE®.

Figure 10:
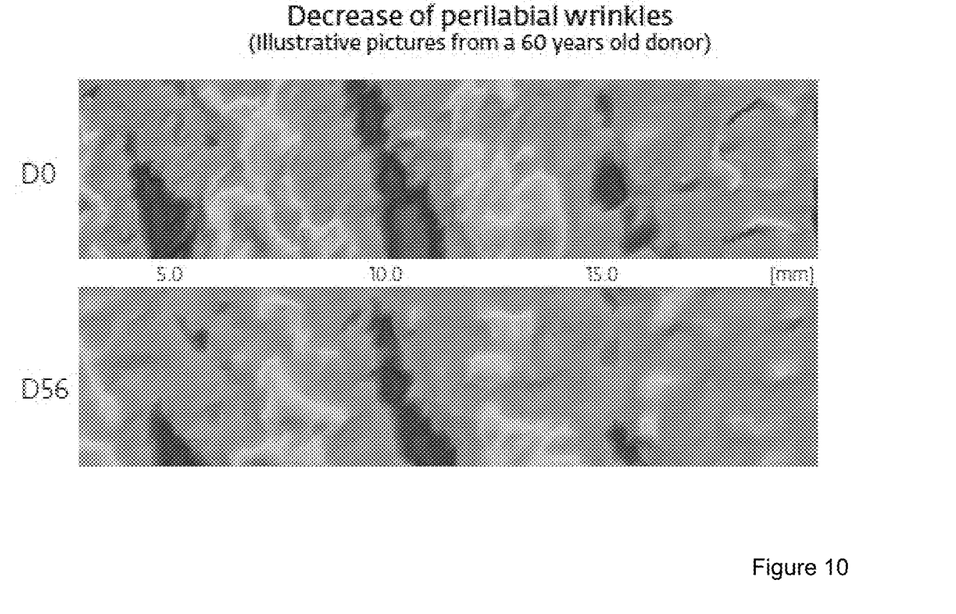
FIG. 10 shows illustrative pictures depicting third comparative testing results of Example 8, according to one or more embodiments of the present disclosure.

The results are shown in FIG. 10. The daily application of the extract of example 2 enables a significant effect for 100% of the volunteers versus placebo in 2 months, with an average reduction of −18%* of the perilabial wrinkles. *p<0.001 Student's t-test c) Self-Assessment of the Skin Benefits All volunteers were asked to assess the benefits of the extract of example 2 for their skin at D56:

76% of the volunteers felt that their skin was more hydrated.

72% of the volunteers felt that their skin was more pleasant and comfortable.

71% of the volunteers felt that their skin was nourished.

EXAMPLE 9: SKIN COMPOSITION AND HYDRATION BENEFITS (CLINICAL TEST)

A double blind clinical evaluation was performed on 20 volunteers (women from 50 to 70 years old, average of 63), with dry legs (corneometry value<35). Volunteers applied the 2% solution from the extract of example 2 or a placebo on their legs twice a day (morning and evening) for 28 days.

a) Improvement of Lipids Organisation

At D0 and D28, Raman spectroscopy was used to assess the quality of lipids conformation in the skin.

Figure 11:
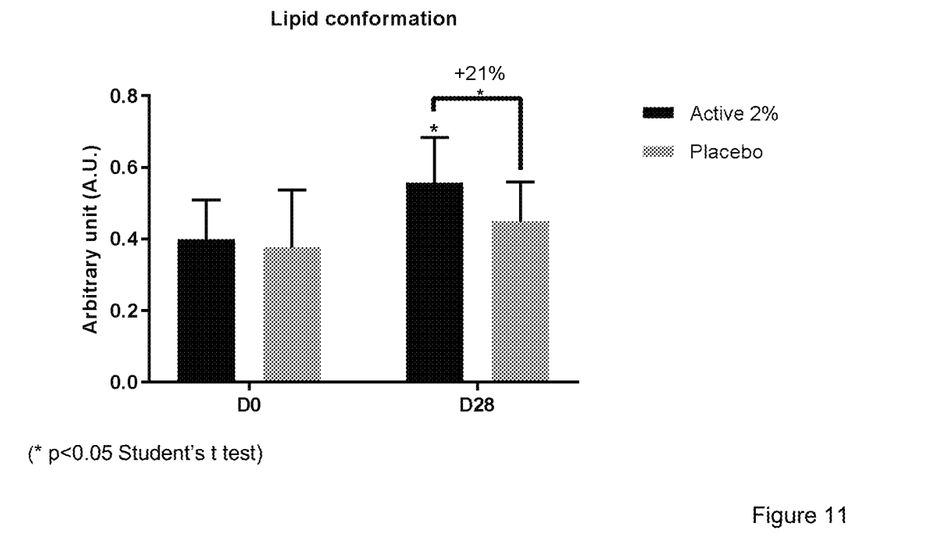
FIG. 11 shows a graph illustrating first comparative testing results for Example 9, according to one or more embodiments of the present disclosure.

The results are shown in FIG. 11. The extract of example 2 shows a significant improvement of the lipids organisation in the skin, of up to +21%, therefore increasing their compactness, and ultimately the barrier function.

b) Increase of Skin Hydration

At D0 and D28, skin hydration was analysed by corneometry.

Figure 12:
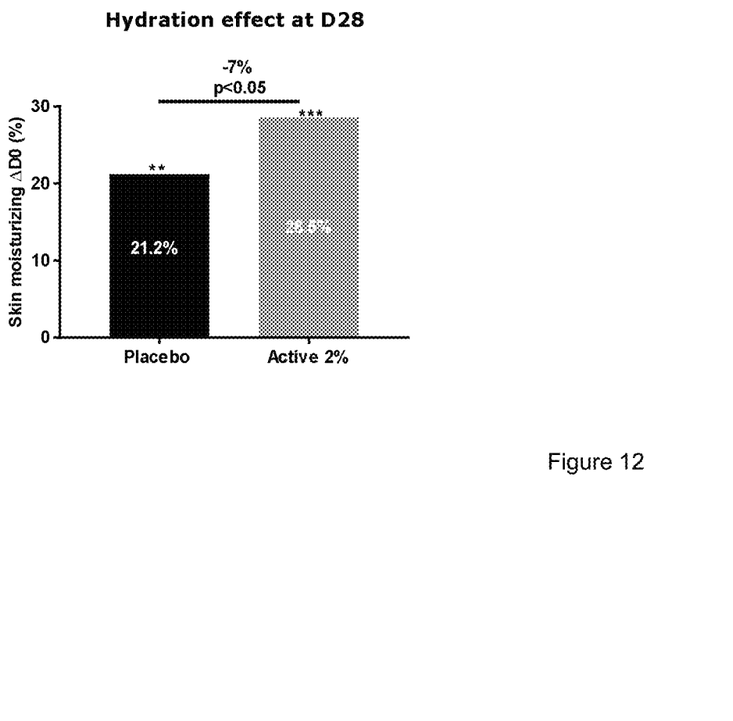
FIG. 12 shows a graph illustrating second comparative testing results for Example 9, according to one or more embodiments of the present disclosure.

The results are shown in FIG. 12. The extract of example 2 shows a significant increase of skin hydration of up to +7.3% on volunteers with dry skin.

EXAMPLE 10: FRAGRANCE BOOSTING BENEFITS (CLINICAL TEST)

To assess the long-lastingness of a fragrance, a clinical test was performed on 20 female volunteers. Volunteers applied twice a day a placebo cream on one of their forearms and the 2% solution from the extract of example 2 on the other forearm for 1 month. Then, on the last day, a fine fragrance (Tom Ford Neroli Portofino) was applied to both of their forearms.

a) Self-Assessment of Long-Lastingness

Volunteers were asked to rank the olfactive intensity of the fine fragrance 2 hours and 4 hours after its application on their skin.

Volunteers observed a significant decrease of fragrance intensity on the forearm treated with placebo while those treated with the extract of example 2 maintained the fragrance intensity after 2 h and 4 h of fragrance application.

Figure 13:
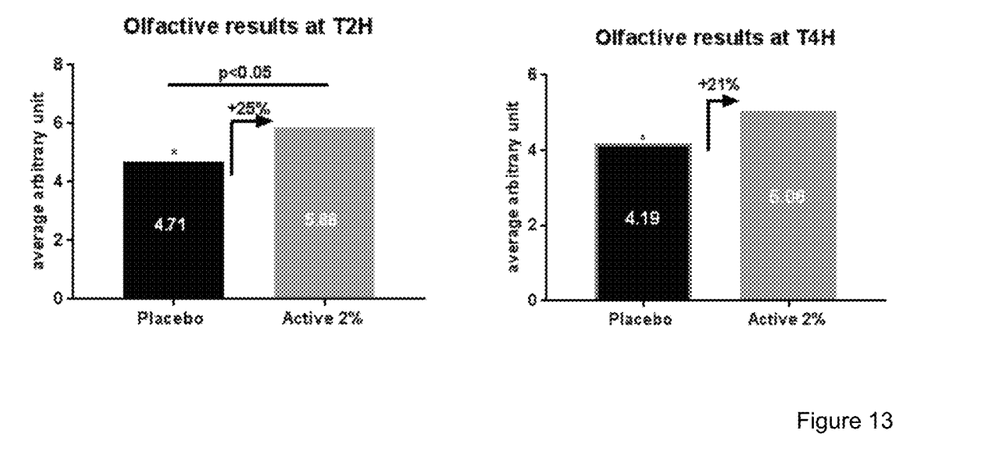
FIG. 13 shows graphs illustrating comparative testing results for Example 10, according to one or more embodiments of the present disclosure.

Comparative results are shown in FIG. 13. The extract of example 2 demonstrates a boosting effect of fragrance long-lastingness by significantly increasing the fragrance olfactive intensity hours after application, by up to +25%.

b) Professional Fragrance Evaluator Opinion

To confirm the benefits of the extract of example 2 in terms of fragrance boosting properties, a professional fragrance evaluator was asked to assess the differences in terms of olfactive properties between the two forearms of the volunteers.

The evaluator came to the conclusion that, the extract of example 2 is emphasizing the fragrance heart and base notes over time, and therefore functions as a fragrance sensuality booster.

EXAMPLE 11: IMPACT ON SEBUM PRODUCTION (CLINICAL TEST)

A double blind and placebo controlled clinical evaluation was carried out on 30 female volunteers (aged 63 to 70, mean age 67±2). The volunteers presented a low level of sebum on their face. All volunteers gave their informed consent sign date the beginning of the study.

The volunteers applied the 2% solution from the extract of example 2 on one side of their face and a placebo on the other side twice a day (morning and evening) for 28 days. At D0 and D28, sebum production on forehead and cheek was analyzed using Sebumeter® (ex Courage—Khazaka Electronic).

Results

It was found that the Vetiver extract induced a significant increase of sebum production after 28 days of application on forehead and cheek with +99% and +78% respectively.

The detailed results are as follows:

|  |  | Forehead | Cheek |
|---|---|---|---|
| Placebo | D 0: Mean +/− SEM ($\mu g/cm^2$) | 33.71 ± 19.49 | 14.29 ± 11.53 |
|  | D 28: Mean +/− SEM ($\mu g/cm^2$) | 50.42 ± 33.15 | 19.81 ± 15.76 |
|  | Δ% D 28 − D 0 (mean) | +50% | +39% |
|  | Student t-test versus D 0 (p) | p < 0.5 | p < 0.1 |
| 2% Vetiver extract | D 0: Mean +/− SEM ($\mu g/cm^2$) | 33.96 ± 19.03 | 17.02 ± 14.16 |
|  | D 28: Mean +/− SEM ($\mu g/cm^2$) | 67.58 ± 35.08 | 30.23 ± 28.12 |
|  | Δ% D 28 − D 0 (mean) | +99% | +78% |
|  | Student t-test versus D 0 (p) | p < 0.001 | p < 0.05 |
|  | Student t-test 2% Vetiver extract versus placebo (p) | p < 0.05 | p < 0.05 |

Therefore, Vetiver extract at 2% is able to reactivate the sebum production that is otherwise drastically reduced on old people.

EXAMPLE 12: ANALYSIS OF EXHAUSTED VETIVER ROOT EXTRACT

Extract Preparation

Exhausted vetiver roots were washed, dried and ground before extraction with water at 60° C. (37.5 g per 1000 g of water) during 6 h, followed by filtration and concentration to obtain 500 g of aqueous extract. The aqueous extract was extracted three times with ethyl acetate (ratio of aqueous extract to total ethyl acetate=1:6). The ethyl acetate extract was evaporated to obtain 2.081 g of a yellow oil.

Fractionation by Centrifugal Partition Chromatography (CPC)

The ethyl acetate extract was fractionated on a CPC instrument FCPE300® (Rousselet Robatel Kromaton) using a column of 303 mL and a two-phase solvent system (n-hexane/EtOAc/methanol/water (10/8/10/8, v/v)).

The CPC chromatogram was monitored at 254, 280, 300, and 360 nm. Fractions of 20 mL were collected over the whole experiment, and combined according to their thin layer chromatography profiles.

NMR Analyses and Identification of the Major Metabolites

The CPC fractions were analyzed by $^{13}C$ NMR at 298 K on a Bruker Avance AVIII-600 spectrometer (Karlsruhe, Germany) equipped with a TXI cryoprobe and compared to metabolites previously reported in the species *Chrysopogon zizanoides*. Additional 2D NMR experiments (HSQC, HMBC, and COSY) were performed on fractions containing putatively identified compounds to confirm the molecular structures proposed by the database at the end of the dereplication process. Also, where necessary, a second CPC fractionation was performed.

The following major metabolites were identified:

(1)

(2)

(3)

(4)

(5)

(6)

(7)

(8)

(9)

(10)

(11)

(12)

(13)

(14)

(15)

(16)

(17)

(18)

(19)

(20)

Of the above metabolites, zizanoic acid (1), oplopanone (6), solanerianone A (8), vetiverianine B (10), valencene-11,12-diol (12), isovalencenic acid (13), and teuhetenone (15) have been previously described.

Substances (2), (3), (4), (5), (7), (9), (11), and (14), on the other hand, have never been described before.

The invention claimed is:

1. A cosmetic composition comprising a carrier and at least one active cosmetic ingredient, wherein the at least one active cosmetic ingredient comprises an extract of exhausted Vetiver root, wherein Vetiver root has previously been processed by steam distillation to provide the exhausted Vetiver root, and further wherein the extract of exhausted Vetiver root comprises:

at least one chemical substance selected from the group consisting of:

(2)

(3)

(4)

(7)

2. The cosmetic composition according to claim 1, wherein the cosmetic composition is a skin care composition.

3. The cosmetic composition according to claim 1, wherein the the extract of exhausted Vetiver root is an aqueous extract of exhausted Vetiver root.

4. A method of stimulating sebum production, of stimulating sebum antimicrobials, of stimulating lipids production, of activating adipocytes volume increase, of improving skin hydration, of boosting skin tonicity, of reducing skin fatigue, of reducing perilabial wrinkles, of replumping skin, and/or of enhancing fragrance long-lastingness, the method comprising the step of: applying the cosmetic composition of claim 1 to human skin.

* * * * *